US011559117B2

(12) United States Patent
Eberra

(10) Patent No.: US 11,559,117 B2
(45) Date of Patent: Jan. 24, 2023

(54) SPRAY AND SNIFF AROMA WRISTBAND

(71) Applicant: Vanessa Gale Eberra, Kansas City, KS (US)

(72) Inventor: Vanessa Gale Eberra, Kansas City, KS (US)

(73) Assignee: Vanessa Gale Eberra, Kansas City, KS (US)

(*) Notice: Subject to any disclaimer, the term of this patent is extended or adjusted under 35 U.S.C. 154(b) by 437 days.

(21) Appl. No.: 16/873,342

(22) Filed: Mar. 25, 2020

(65) Prior Publication Data
US 2020/0305559 A1 Oct. 1, 2020

Related U.S. Application Data

(60) Provisional application No. 62/919,741, filed on Mar. 27, 2019.

(51) Int. Cl.
A44C 5/00 (2006.01)
A44C 15/00 (2006.01)
A61M 11/00 (2006.01)

(52) U.S. Cl.
CPC .......... A44C 5/0023 (2013.01); A44C 15/002 (2013.01); A61M 11/007 (2014.02)

(58) Field of Classification Search
CPC ..... A44C 5/0023; A44C 15/002; A44C 5/003; A61M 11/007
USPC ......................................... 63/1.11, 1.15, 1.14
See application file for complete search history.

(56) References Cited

U.S. PATENT DOCUMENTS

| | | | | |
|---|---|---|---|---|
| 1,445,528 A * | 2/1923 | Marsh | .................... | A44C 5/003 224/236 |
| 5,217,143 A * | 6/1993 | Aitken | ................ | A44C 15/002 206/823 |
| 5,413,126 A * | 5/1995 | Revson | .................... | A45C 1/04 132/273 |
| 5,826,598 A * | 10/1998 | Meehan | ................... | A45D 8/34 132/273 |
| D605,276 S * | 12/2009 | Beardmore | ................. | D23/366 |
| 8,668,080 B1 * | 3/2014 | Kazanchyan | .......... | A45C 11/16 206/6.1 |
| 9,472,930 B2 * | 10/2016 | Lake-Maiorana | ... | H02G 3/0462 |
| 2002/0084279 A1 * | 7/2002 | Lickstein | ............... | A47K 10/42 221/24 |

(Continued)

Primary Examiner — Justin M Jonaitis

(57) ABSTRACT

A wearable aroma emitting device housing a refillable, removable atomizer spray bottle. The device comprising a circular tubular housing that can be impregnated with aromatic substance and emanate therefrom. An elastic band with an attached pocket is located within the chamber of the tubular housing. Alternatively, the tubular housing can be made of elasticized material. The pocket houses the atomizer spray bottle which can be filled with fragrance or scent. The pocket opening is covered with overlapping elasticized material attached to the tubular housing, which allows easy access to the atomizer spray bottle. The aroma device can be worn on the wrist; when the atomizer spray bottle is removed, it can be worn in the hair for scent. In another embodiment of the present invention, an ornamental three dimensional stuffed structure is located on a portion of the tubular housing. The atomizer spray bottle is housed within the stuffed structure.

16 Claims, 4 Drawing Sheets

(56) References Cited

U.S. PATENT DOCUMENTS

| | | | |
|---|---|---|---|
| 2004/0111071 A1* | 6/2004 | Powers | A47K 5/122 604/310 |
| 2014/0110445 A1* | 4/2014 | Eisner | A45F 5/00 224/222 |
| 2018/0071466 A1* | 3/2018 | White | A44C 5/003 |
| 2019/0239601 A1* | 8/2019 | Frietsch | A41D 27/202 |

* cited by examiner

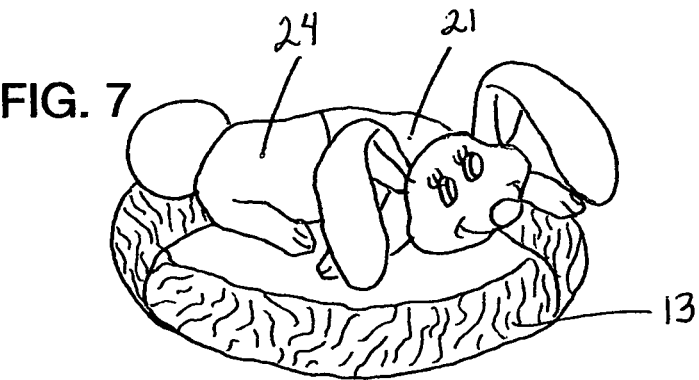
FIG. 7
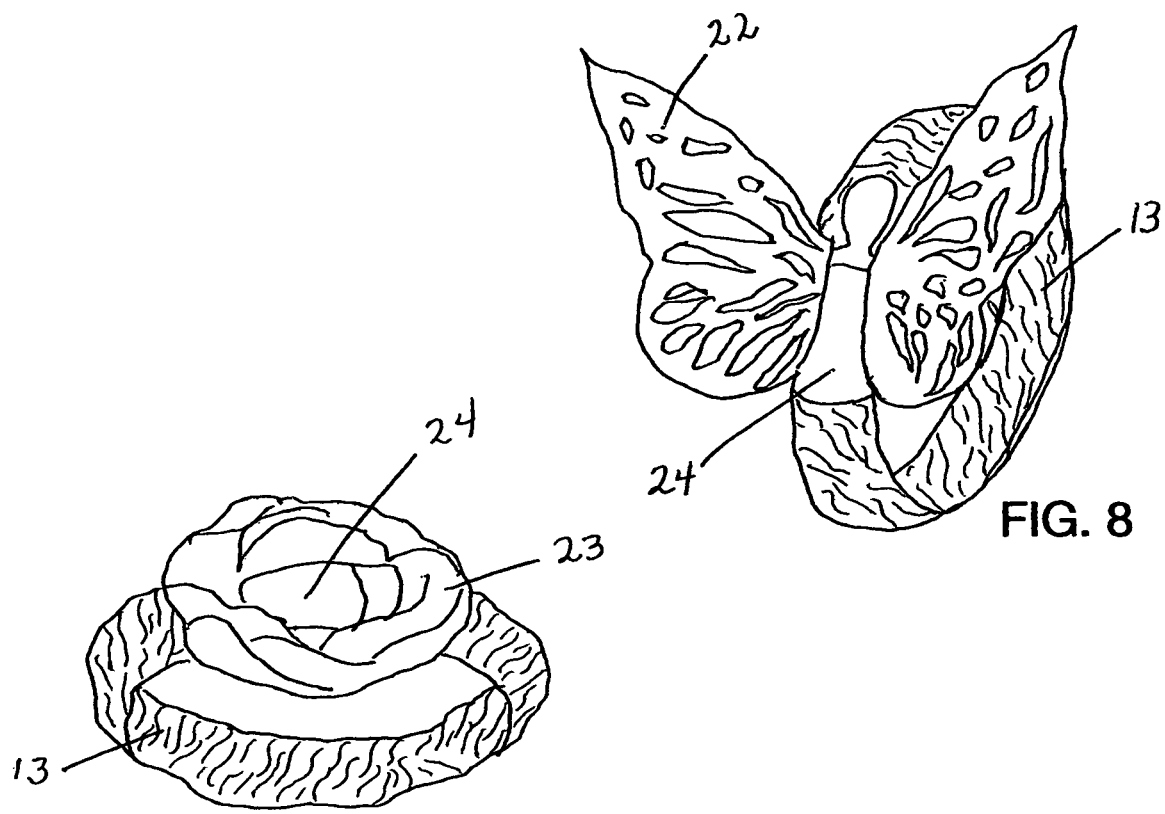
FIG. 8
FIG. 9

SPRAY AND SNIFF AROMA WRISTBAND

BACKGROUND

Human beings have five basic senses; touch, sight, smell, hearing and taste. Of these five senses, the sense of smell is very powerful. The ability to smell can be critical, in that it may alert us to danger in the event of smoke, harmful chemicals, and even spoiled foods; and when we experience unpleasant smells, we use favorable scents to help eliminate or cover up the foul odor. We also use the ability to smell to help provide aid in our mental and physical wellness with the use of certain therapeutic scents. There are also certain familiar and pleasant smells that may contribute to us feeling good, recalling precious moments and aid in sexual attraction. Some of our everyday choices are considered due to our sense of smell because, for the most part, we all want to feel, look and smell good.

The home air freshening sector and fragrance such as perfumes, colognes and body sprays are multi-billion dollar industries because the ability to smell, strongly affects all aspects of our lives. We live in a society where not only do we want to smell good, but we also have a desire for a pleasant smelling environment, which causes us to spend money on various scent devices such as scented candles and oils, we use in candle warmers and diffusers. We use scented plugins for our electrical outlets and automatic scent sprayers for our table tops and walls. These devices to name a few helps to enhance or cover-up the unpleasant smells in our homes and workplaces. We also use essential oil diffusers, vent clip-ons and decorative air fresheners that hangs off the rearview mirrors in our automobiles.

When we leave our pleasant smelling environment or scent controlled area and venture out into the general public where we are at the mercy of whatever odors awaits us. Fouls odors are inevitable. We may have to experience crowded stuffy rooms, long customer service lines cascaded with a variety of scents and smells due to body odors, and at some point in time, we may have too endure a smelly public restroom.

We are also at the mercy of the air quality when we travel in confined spaces such as by car, air, train, bus or by ship. Whatever the reason or circumstances, unpleasant odors are a part of life that affects many of us.

It would be beneficial to have a wearable aroma emitting device which could transform an individual's immediate personal space into their own pleasant oasis wherever they are, tailored with their favorite personal fragrance or scent.

The wearable aroma emitting device can be used in a variety of ways. It can be sprayed with the wearer's personal fragrance, or any aroma substance of their choosing, so the wearer could just sniff the wearable aroma emitting device when trying to avoid a foul or pungent odor. The wearable aroma emitting device is configured as a wristband, so a pleasant aroma, at anytime, is literally at arms length.

The wearable aroma emitting device can be sprayed in partial or saturated with the wearer's favorite scent or fragrance so that it permeates strongly throughout their immediate personal space, filling their area with a pleasant aroma.

The wearable aroma emitting device is also very convenient because it houses a atomizer spray bottle that is literally at the wearer's fingertips. The wearer does not have to search around in their purse or pocket to find a bottle or container of their favorite cologne, perfume, body spray, or any preferred scent; having a wearable aroma emitting device makes it easy for the wearer to discreetly spray perfume on their person for a blast of scent, or in the air.

A wearable aroma emitting device is great for kids, especially preteens. They could enjoy fun and creative custom scents such as vanilla creme cookies, root beer float, or cinnamon candy apple. These custom scents, to name a few can be sprayed on their person or in the air to enjoy the aroma.

There are related jewelry type devices that emit scent such as the aromatherapy diffuser bracelet which works by adding drops of essential or fragrance oil on a small felt or cotton pad and placed inside the bracelet locket. A disadvantage of using pure essential oils (if used) must be properly diluted are it can be harmful if used topically. Also, diffuser bracelets only uses a small surface to carry the scent; whereas the entire surface area of the present invention can be uses for receiving scent or fragrance, and can be used topically without a mixture calculation. In addition, the present invention houses a atomizer spray bottle, that comes with added benefits of allowing the wearer to spray their person for additional scent, spray their immediate personal space for aroma or to spray in order to avoid a foul odor.

Another related jewelry type device that emit scent is the lava bead bracelets which also uses essential or fragrance oils. Lava beads have porous surfaces and the oils are absorbed to give off scent. The same advantages and disadvantages in comparing this related jewelry device to the present invention would be the same as to the diffuser bracelet, with the small exception to the essential or fragrance oils that are used can be applied to the entire surface area of the lava bead bracelet.

There are also jewelry pieces such as rings, necklaces, bracelets and brooches that are design to emit perfume or the preferred scent of the wearer. These particular jewelry pieces houses a porous material which liquid scent is applied, allowing the jewelry to emit a scent. The present invention also emit perfume, but it also has the advantage of allowing the wearer to spray fragrance on their person, in the air for aroma or to spray to avoid a foul odor.

Some other related examples would be in the prior art of the following patents: U.S. Pat. No. D605,276S1 describes an aromatherapy elastic band having a pocket for a aromatherapy pad. This prior art design looks similar to the present invention, but is different in many ways. The present invention has a pocket attached to a elastic band within the inner chamber of the tubular housing, accessible through a opening in the tubular housing. The pocket houses a atomizer spray bottle that holds a aromatic substance such as fragrance or scent. The wearer can utilize the atomizer spray bottle and spray scent on their person or in the air for aroma. Also, the prior art is designed to work with essential oils whereas the present invention primarily uses fragrances such as perfumes, cologne, body sprays and other scents that can be used topically, and without being diluted.

Another prior art is U.S. Pat. No. 5,826,598A which describes a scented hair accessory that can also be worn on the wrist, having a pocket that can house scent material. Some aspects of this prior art is similar to the present invention such as the tubular housing and the elastic band within the inner chamber of the tubular housing. The present invention is different in that the elastic band within the inner chamber has an attached pocket that houses a atomizer spray bottle that can be filled and refilled with aromatic substance such as fragrance and scent for spraying on the wearer or in the air. Also, the ornamental three dimensional stuffed structure which houses a atomizer spray bottle as described in the present invention is quite different when comparing it to the ornamental structure of the prior art.

Another prior art is U.S. Pat. No. 6,105,837A which describes a wearable article carrier. A band that can be worn on the body, and a pouch member detachably connected to the band. This prior art may have similar components in comparing it to the present invention, but the overall usage and design is very different. The prior art is described as something designed to hold and carrier items. The present invention was designed to emit and house aromatic substance, with the use of a atomizer spray bottle.

While there are numerous wearable storage devices, and wearable scent emitting devices published and on the market that may have similar elements or characteristics to the present art, the over all present art is unique in its combined functions, and also in some individual features and purposes.

The advantages of the present invention is that a wearable aroma emitting device could provides a simplistic and unique way of enhancing the wearer's present body scent. It also allows the wearer to be able to discreetly spray aroma in their immediate personal space. The wearable aroma emitting device also houses a refillable and removable atomizer spray bottle that can be filled and refilled with the wearer's favorite perfume, cologne, body spray, or any scent of the wearer's choosing.

The outer tubular housing of the wearable aroma emitting device, is made of porous material that can hold and emanate scent. When the wearable aroma emitting device is sprayed with scent, it can help the wearer avoid foul odors in their immediate personal space by just sniffing the wristband and enjoying the fragrance or scent until the unpleasant odor has subsided or until the wearer has cleared the area. When the wearer choose to use the atomizer spray bottle, only the pump head is exposed, so that the wearer can discreetly spray aroma into the air for pleasure, or in the air to avoid a foul odor. The wearer can also spray on their person for a stronger blast of scent or fragrance when needed.

If the wearer is sensitive to perfumes and can not have direct skin contact with perfumes and the like, the wearable aroma emitting device can be partially sprayed with their favorite scent, allowing the wearer to still experience the benefits of the present invention.

For the wearer who is extremely skin sensitive to fragrance and the like. They have the option not to spray the wearable aroma emitting device and only use the removable and refillable atomizer spray bottle to spray their immediate personal space when a foul odor is present or just to enjoy a pleasant aroma. The wearable aroma emitting device can be stylish and fashionable due to all the possible fabric patterns, materials and colors that can be used in constructing the wearable aroma emitting device, accentuating the wearer's wardrobe.

When the wearable aroma emitting device is sprayed it will retain scent over a period of time for the enjoyment of the wearer until the scent is washed out.

The wearer also has the option to spray the wearable aroma emitting device for scent and remove the refillable spray bottle from the pocket, and use the wearable aroma emitting device to pull back the wearer's hair into a ponytail, bringing the wearer's favorite scent to their hair.

Therefore, a need exist for the present invention. It provides a way to discreetly intensify or boost the pleasant smelling aroma of the wearer's perfume, cologne, body spray or any scent of their choosing. The present invention would also be beneficial for wearers who may have skin sensitivity to perfumes and the likes. The wearer could use only the atomizer spray bottle and spray aroma in the air, avoiding skin contact with the perfume.

The wearable aroma emitting device provides the convenience of being able to inconspicuously spray scent when needed, either on the wearer's person to enhance their body fragrance or the wearer can spray scent in their immediate personal space when a foul odor is present.

The wearable emitting device can also be partially sprayed or completely saturated with the scent or fragrance of the wearer's choosing, amplifying the aroma in their immediate personal space.

The wearable emitting device houses a refillable and removable atomizer spray bottle that can be filled and refilled with the wearer's favorite scent or fragrance.

The wearable aroma emitting device could accessorize any wardrobe due to the variety and unlimited fabric material that can be used to construct the present invention such as the use of solid colors, prints, and patterns, the wearable aroma emitting device can be quite fashionable.

BRIEF SUMMARY OF THE INVENTION

The present invention is described as a wearable aroma emitting device that houses aromatic substance such as perfume, cologne, body spray or any scent of the wearer's choosing. The outer tubular housing of the wearable aroma emitting device is made of porous material, allowing the wearable aroma emitting device to receive and emanate aromatic substance. A pocket attached to a elastic band within the inner chamber of the wearable aroma emitting device, houses a removable and refillable atomizer spray bottle that can be filled and refilled with any fragrance or scent of the wearer's choosing.

The atomizer spray bottle is housed within the pocket and the pump head of the spray bottle protrudes through an opening in the outer tubular housing of the wearable aroma emitting device and is concealed behind a elasticized closure attached to the outer tubular housing of the wearable aroma emitting device. This configuration allows the spray bottle to be used inconspicuously. The wearable aroma emitting device can help boost or intensify the scent of the wearer, and can combat or help avoid foul odors in their immediate personal space. The wearable aroma emitting device can also be a benefit to wearers who can not have direct skin contact with fragrance and the like, by just utilizing the atomizer spray bottle. The wearable aroma emitting device can be easily cleaned of fragrance or scent, and can enhance and accentuate any wardrobe due to the variety of material, colors and patterns design that can be used to construct the wearable aroma emitting device.

In another embodiment of the present invention an ornamental three dimensional stuffed structure is located on a portion of the tubular housing of the wearable aroma emitting device. The stuffed structure can be a representation of a stuffed animal, plant/flower, insect/bug or various shapes such as a heart, star. The representation of the stuff structure is not limited to any place, person or thing. The atomizer spray bottle can be housed within a inner chamber of the three dimensional stuffed structure or within an external pocket attached to the three dimensional stuffed structure.

This particular embodiment of the wearable aroma emitting device would be great for preteens because of the unique and fun design of the three dimensional stuffed structure housing the atomizer spray bottle. The preteens could also enjoy creative custom scents that they could spray on their person or in the air to enjoy the aroma. Optionally, the stuffed ornamental structure can be sprayed with scent.

BRIEF DESCRIPTION OF THE DRAWINGS

FIG. 4 depicts an example of a front view of the refillable and removable atomizer spray bottle with no cap according to the embodiment described herein with.

FIGS. 7-9 depicts other examples of another preferred embodiment of the wearable aroma emitting device of the present invention.

DETAILED DESCRIPTION OF THE INVENTION

Figure 1:
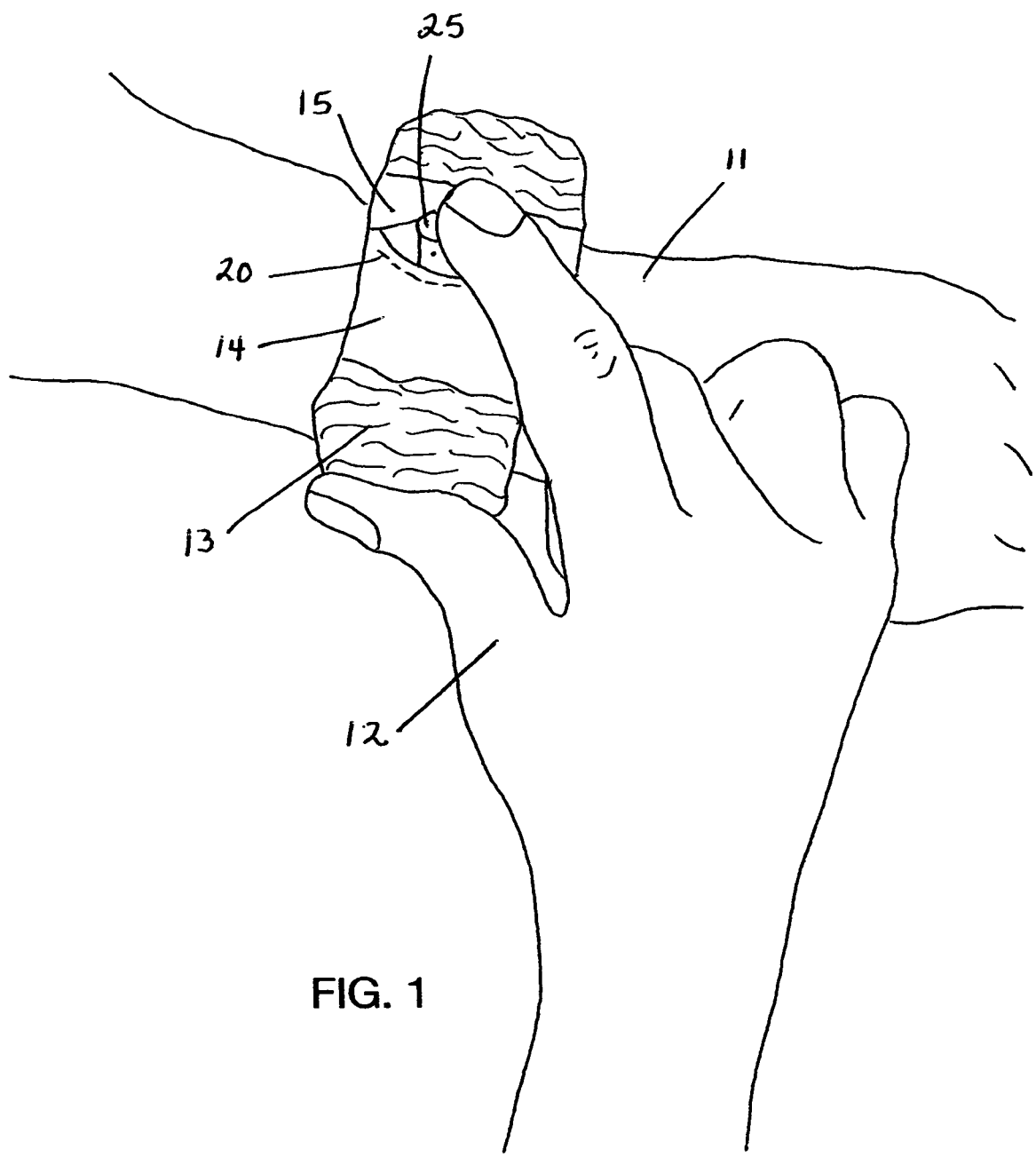
FIG. 1 illustrates the wearable aroma emitting device on a wrist giving a perspective view of an example of the device opening within the outer tubular housing, represented by dotted lines, the overlapping elasticized closure pulled apart exposing the pump head of the refillable and removable atomizer spray bottle and the demonstration of the use of the atomizer spray bottle according to the embodiments described herein.

The present Invention provide a new and unique way of emitting fragrance and the like for enhancing personal body scent, and combating or avoiding odors in ones immediate personal space. The wearable aroma emitting device is comprised of a circular and porous tubular housing having an opening on the outer portion of the tubular housing allowing access to the inner chamber of the tubular housing. The opening is concealed by two partially overlapping elasticized material attached to the outer tubular housing. Alternatively, the closure for the opening can be made out of one piece of material.

The porous nature of the material used for the tubular housing allows the wearable aroma emitting device to emit fragrance after it has been impregnated with fragrance or scent, which will help boost or intensify the scent of the wearer and to help add a more pleasant and favorable scent to their immediate surroundings.

Within the inner chamber of the tubular housing of the wearable aroma emitting device is a elastic band making the tubular housing expandable. The elastic band is shorter in length than the tubular housing, allowing the tubular housing material to gather around the elastic band. Alternatively, the tubular housing may be comprised of elasticized material, making it unnecessary for the inner elastic band.

A pocket is attached to the elastic band within the inner chamber of the tubular housing of the wearable aroma emitting device. The open ended portion of the pocket is positioned right below the opening in the tubular housing. The upper edge of the open ended portion of the pocket is attached to the lower edge of the opening in the tubular housing, this helps keep the pocket anchored in one spot. Alternatively, if there is no inner elastic band, a pocket can be attached directly onto a portion of the outer tubular housing of the wearable aroma emitting device, concealed by a closure of one or two pieces of porous elasticized material attached to the outer tubular housing. Another option is having the pocket remain visible on the outer tubular housing of the wearable aroma emitting device with a closure of conventional methods such as a zipper, snap, button or velcro.

The pocket houses a refillable and removable atomizer spray bottle. The cap of the atomizer spray bottle is removed before placing it into the pocket of the wearable aroma emitting device, this is for convenience in helping the wearer be discreet when spraying aroma. The pump head of the atomizer spray bottle is positioned through the opening in the outer tubular housing of the wearable aroma emitting device, and is concealed by the two partially overlapping elasticized material that serves as a closure attached to the outer tubular housing of the wearable aroma emitting device. The body or reservoir of the atomizer spray bottle remain housed in the pocket within the inner chamber of the wearable aroma emitting device.

The atomizer spray bottle is accessible and ready to use just by moving the overlapping elasticized material apart. The atomizer spray bottle may be filled and refilled with perfume, cologne, body spray or any scent of the wearer's choosing. The atomizer spray bottle can be used inconspicuously due to its position within the wristband. The wearer has the option to spray fragrance on their person, in the air to enjoy or when a foul odor is present.

The wearable aroma emitting device can hold scent for a extended period of time and can be easily cleaned of the fragrance.

The wearable aroma emitting device is also suitable for wearers who can not have direct skin contact with fragrance or the like.

The present invention can also enhance and accentuate any wardrobe due to the variety of fabric colors and pattern designs and material that can be used to construct the wearable aroma emitting device.

In another preferred embodiment of the present invention an ornamental three dimensional stuffed structure is located on a portion of the outer tubular housing of the wearable aroma emitting device. The outside material of the stuff structure can be made fabric such as plush, textiles and other cloths and material related to furry and non-furry stuffed toys. The inside filling of the stuffed structure can be cotton, synthetic fibers or any similar material that may help keep its shape. If eyes or nose is present, they can be made of various plastics. The stuffed structure can be a representation of a animal, plant/flower, insect/bug or various shapes such as a heart or star and is not limited to these described representations. The atomizer spray bottle can be housed within a inner chamber of the three dimensional stuffed structure or housed within a external pocket attached to the three dimensional stuffed structure. The closure for the inner chamber or external pocket can be of conventional means such as a flap, snap, zipper or velcro.

In this embodiment the atomizer spray bottle may be removed from the stuffed structure when the wearer is ready to spray. The tubular housing of the wearable aroma emitting device can be slightly narrow in width in comparison to the present invention and the tubular housing may not need a elastic band within the inner chamber if the tubular housing is made of elasticized material.

This embodiment of the wearable aroma emitting device would be great for kids, especially preteens because of the unique and fun designs of the three dimensional stuffed structural attachment to the wearable aroma emitting device's outer tubular housing. In combination with the atomizer spray bottle that would allow the wearer to enjoy creative custom scents that the wearer could spray on their person or in the air to enjoy the aroma. Optionally, the stuffed structure can be sprayed with scent.

The terminology used herein is for the purpose of describing particular embodiments only and is not intended to be limiting of the invention.

It is understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

The present disclosure is to be considered as an exemplification of the invention, and is not intended to limit the invention to the specific embodiments illustrated by the figures or description below.

The present invention will now be described by referencing the appended figures representing preferred embodiments.

FIG. 1 illustrates a perspective view of an example of the wearable aroma emitting device according to the embodiments of the present invention. The wearable aroma emitting device 13 stretches around the accompanying illustration of a wrist 11. The tubular housing of the wearable aroma emitting device 13 is made of porous fabric, but not limited to solely porous fabrics. The tubular housing of the wearable aroma emitting device 13 may also be made of elasticized porous fabric or any type of material adapted to fit around a wrist 11 and able to hold and emanate scent, and configured for a removable and refillable spray bottle 16 to be housed. The outer tubular housing of the wearable aroma emitting device 13 comprising of two pieces of horizontal overlapping porous material configured for a closure 14 and 15 made of elasticized fabric. The overlapping porous closure 14 and 15 conceals an opening 20 in the outer tubular housing of the wearable aroma emitting device 13. The circumference of the opening 20 is larger than the outer circumference of the atomizer spray bottle 16. The opening 20 is position above the open ended portion of a pocket 18 (not shown) sewn 19 onto a elastic band 17 within the inner chamber of the tubular housing of the wearable aroma emitting device 13.

The upper edge of the open ended portion of the pocket 18 is attached to the lower edge of the opening 20 in the outer tubular housing of the wearable aroma emitting device 13. The refillable and removable atomizer spray bottle 16 is housed within the pocket 18.

The pump head 25, of the atomizer spray bottle 16 is positioned through the opening 20 in the outer tubular housing of the wearable aroma emitting device 13 and is concealed by the overlapping elasticized closure 14 and 15. The elasticity of the fabric for the closure 14 and 15 allows for the pump head 25 of the atomizer spray bottle 16 to be easily accessible for spraying discreetly as demonstrated by the accompanying illustration of a hand 12. While elasticized fabric is preferred for the closure 14 and 15, it is not limited to this material.

Optionally, the atomizer spray bottle 16 can be housed between the outer tubular housing of the wearable aroma emitting device 13 and the elasticized closure 14 and 15.

Another option is to have a pocket 18 attached to the outer tubular housing of the wearable aroma emitting device 13 to house the atomizer spray bottle 16. The pocket 18 can be closed and accessible by means of a zipper, button(s), flap(s), snap(s) or any other conventional means of closures.

Figure 2:
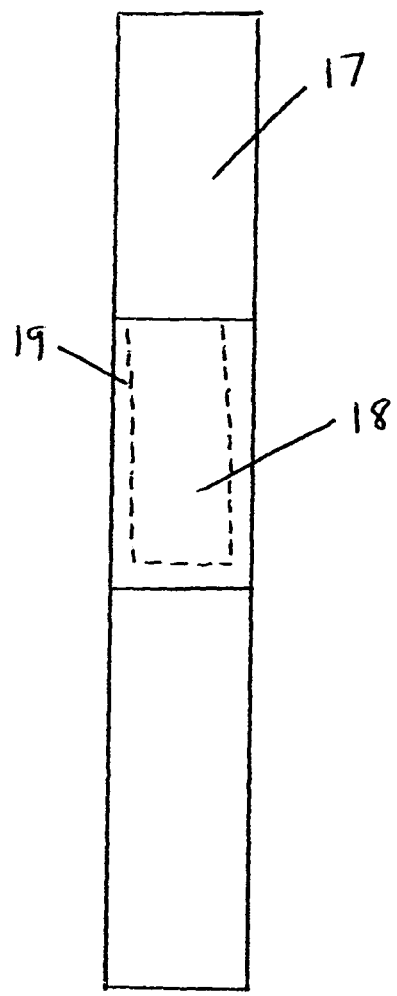
FIG. 2 depicts the elastic band with sewn on pocket giving a perspective view of the embodiment described herein.

FIG. 2 depicts a elastic band 17 with a pocket 18 made from elasticized material, but not limited to this material, is sewn on with thread 19. The pocket 18 is not limited to being sewn on by thread 19, or glued on. The elastic band 17 is located within the inner chamber of the tubular housing of the wearable aroma emitting device 13 and allows the wearable aroma emitting device 13 to stretch comfortably around the wrist 11.

The pocket 18 houses the removable and refillable atomizer spray bottle 16. The opening 20 on the outer tubular housing of the wearable aroma emitting device 13, above the open ended portion of the pocket 18, that is located within the inner chamber of the outer tubular housing of the wearable aroma emitting device 13, is configured for the pump head 25 of the refillable and removable atomizer spray bottle 16 to be to positioned through the opening 20. The pump head 25 of the atomizer spray bottle 16 is easily accessible and remain concealed by the overlapping elasticized closure 14 and 15 attached to the outer tubular housing of the wearable aroma emitting device 13 until the atomizer spray bottle is ready to be used.

The elastic band 17 with an attached pocket 18 does not have to be used if the tubular housing of the wearable aroma emitting device 13 is made of elasticized material. The atomizer spray bottle 16 can be housed and concealed between the outer tubular housing of the wearable aroma emitting device 13 and the overlapping elasticized closure 14 and 15.

Figure 3:
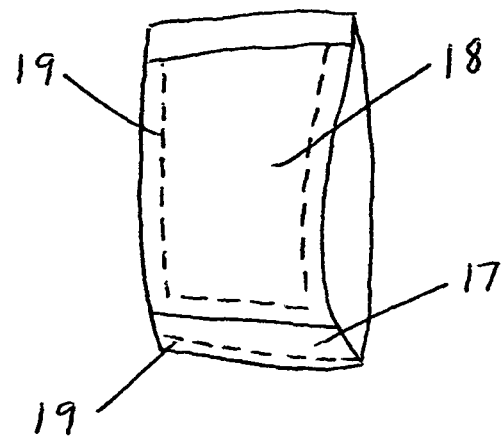
FIG. 3 depicts the elastic band with sewn on pocket sewn together at the open ends giving a perspective view according to the embodiment described herein.

FIG. 3 depicts a elastic band 17 with sewn on pocket 18 by thread 19. The elastic band 17 is located within the inner chamber of the tubular housing of the wearable aroma emitting device 13. The ends of the elastic band 17 is sewn together with thread 19.

Figure 4:
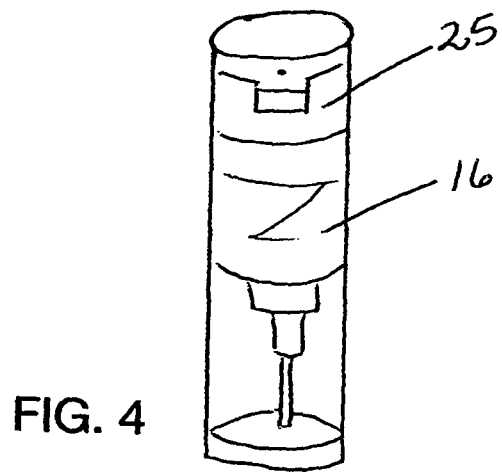

FIG. 4 depicts a refillable and removable atomizer spray bottle 16 used to spray fragrance or scent of the wearer's choosing. The refillable and removable atomizer spray bottle 16 is not limited to any material. The atomizer spray bottle 16 may include parts such as a pump head 25, orifice insert, actuator, stem, gasket, spring cup, spring and dip tube.

Figure 5:
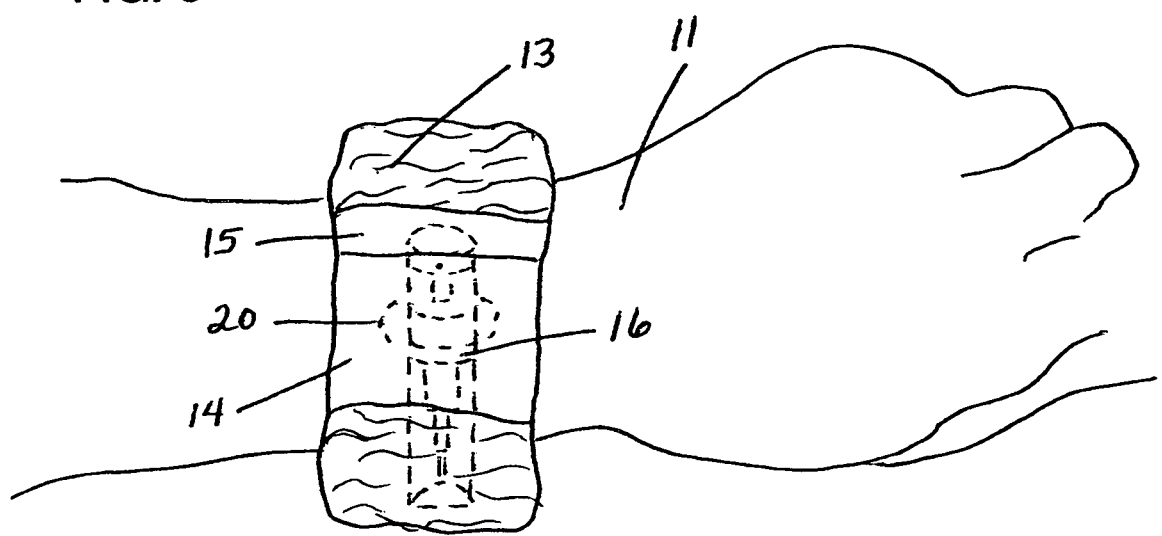
FIG. 5 depicts the wearable aroma emitting device on a wrist giving a perspective view of an example of the device concealing a refillable and removable atomizer spray bottle represented by dotted lines, in a pocket (not shown) within a inner chamber (not shown) of the wearable aroma emitting device, and the opening within the outer tubular housing of the wearable aroma emitting device, represented by dotted lines concealed underneath a overlapping elasticized closure according to the embodiments described herein.

FIG. 5 illustrates the wearable aroma emitting device 13 stretching around the accompanying illustration of a wrist 11. The refillable and removable atomizer spray bottle 16 represented by dotted lines, is housed in a pocket 18 (not shown) attached to a elastic band 17 (not shown) within the inner chamber of the tubular housing of the wearable aroma emitting device 13. The overlapping elasticized closure 14 and 15 is attached to the outer tubular housing of the wearable aroma emitting device 13, concealing the opening 20 within the outer tubular housing of the wearable aroma emitting device 13. The opening 20 is represented by dotted lines.

Figure 6:
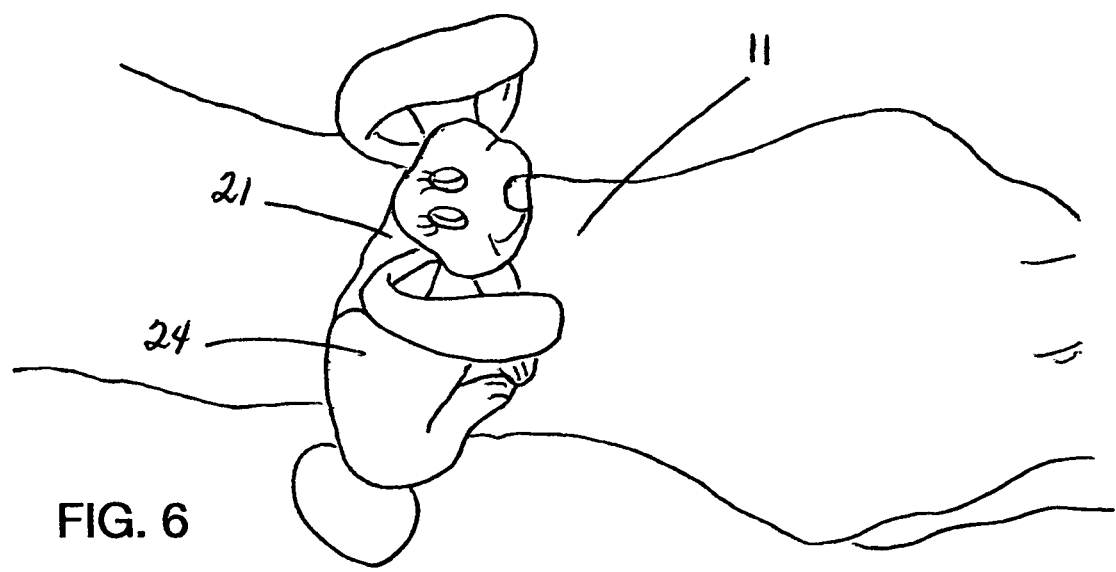
FIG. 6 depicts another preferred embodiment of the wearable aroma emitting device of the present invention on a wrist.

FIG. 6 depicts another preferred embodiment of the wearable aroma emitting device of the present invention. A ornamental three dimensional stuffed structure representing a floppy eared bunny rabbit 21 is attached to the outer tubular housing (not shown) of the wearable aroma emitting device, and is stretched around the accompanying illustration of a wrist 11. The outside covering material of this preferred embodiment can be made of fabric such as plush, textile, cloth or any other related material. The inside stuffing material can be cotton, synthetic fiber, or any other related material that will allow the stuffed structure to hold its shape. The eyes and nose can be made of plastic or similar material. The ornamental three dimensional stuffed structure representing a floppy eared bunny rabbit 21 houses a atomizer spray bottle 16 (not shown) within an external pocket 24 located on the back portion of the stuffed structure representing a floppy beard bunny rabbit 21. Optionally, the external pocket 24 can have a closure of conventional means such as a zipper, snap, button or velcro. Alternatively, the atomizer spray bottle 16 can be housed within a inner chamber of the stuffed structure embodiments, with a closure of conventional means such as a zipper, snap, button or velcro.

FIG. 7 depicts another view of the ornamental three dimensional stuffed structure representing a floppy eared bunny rabbit 21 attached to the outer tubular housing of the wearable aroma emitting device 13 with an attached external pocket 24 located on the back portion of the stuffed structure representing a floppy eared bunny rabbit 21. The external pocket 24, houses a atomizer spray bottle 16 (not shown). The tubular housing of the wearable aroma emitting device 13 is narrower in width compared to the present invention.

FIG. 8 depicts another example of a preferred embodiment of the wearable aroma emitting device of the present invention. A ornamental three dimensional stuffed structure representing a butterfly 22 attached to the outer tubular housing of the wearable aroma emitting device 13 with an attached external pocket 24 located on the back portion of the structure that makes up the body of the butterfly 22. The external pocket 24 houses a atomizer spray bottle 16 (not shown). The tubular housing of the wearable aroma emitting device 13 is narrower in width compared to the present invention.

FIG. 9 depicts another example of a preferred embodiment of the wearable aroma emitting device of the present invention. A ornamental three dimensional stuffed structure representing a flower 23 attached to the outer tubular housing of the wearable aroma emitting device 13 with an attached external pocket 24 located in the center of the flower 23. The external pocket 24 houses a atomizer spray bottle 16 (not shown). The tubular housing of the aroma wristband 13 is narrower in width compared to the present invention.

While preferred materials for elements have been described, the device is not limited by these material. Materials such as plastic, porous fabric, elastic material, plush, textile, cloth and other materials may comprise some or all of the elements of the aroma device in the embodiments of the present invention.

What is claimed:

1. A wearable aroma emitting device that houses a aromatic substance comprising:
   a circular tubular housing having an opening on a outer portion of said tubular housing;
   said tubular housing including a closure for concealing said tubular housing opening comprising two pieces of elasticized material;
   an elastic band with an attached pocket within an inner chamber of said tubular housing;
   said pocket having an open end and a closed end and connected to said tubular housing opening;
   a atomizer spray bottle configured for holding a aromatic substance; and said pocket configured for removably housing said atomizer spray bottle.

2. The wearable aroma emitting device of claim 1, wherein said tubular housing opening accommodates access to the inner chamber within the said tubular housing.

3. The wearable aroma emitting device of claim 1, wherein said two pieces of elasticized material are configured for overlapping and attached to said tubular housing.

4. The wearable aroma emitting device of claim 1, wherein said tubular housing is made of porous material.

5. The wearable aroma emitting device of claim 1, wherein said tubular housing is made of elasticized material.

6. The wearable aroma emitting device of claim 1, wherein said elastic band is shorter in length in comparison to said tubular housing configured for gathering said tubular housing around said elastic band; and said elastic band is narrower in width in comparison to the width of said tubular housing.

7. The wearable aroma emitting device of claim 1, wherein said pocket is attached to said elastic band whereas:
   at least a portion of said pocket closed end is located within said inner chamber of said tubular housing and;
   at least a portion of said pocket open portion is accessible through said tubular housing opening.

8. The wearable aroma emitting device of claim 1, whereas a lower edge of said tubular housing opening is attached to an upper edge of said open end portion of the pocket, allowing said pocket to remain anchored in one place within said inner chamber.

9. The wearable aroma emitting device of claim 1, wherein said atomizer spray bottle is refillable, and can be filled with said aromatic substance such as fragrance or scent of the user's choosing.

10. The wearable aroma emitting device of claim 1, wherein said atomizer spray bottle comprising a pump head, a spring, a dip tube and a reservoir.

11. The wearable aroma emitting device of claim 10, wherein said pump head is connected to said dip tube, and said dip tube is connected to said reservoir for holding said aromatic substance and said pump head configured for spraying a amount of said aromatic substance when pressed.

12. The wearable aroma emitting device of claim 10, wherein said pump head of said atomizer spray bottle is positioned through said tubular housing opening, and said reservoir of said atomizer spray bottle is positioned in said pocket within the said inner chamber.

13. The wearable aroma emitting device of claim 10, wherein said pump head is concealed beneath said overlapping elasticized closure attached to said tubular housing, allowing said atomizer spray bottle to be easily accessible; the user can easily remove said refillable atomizer spray bottle or spray inconspicuously on their person or in the air.

14. The wearable aroma emitting device of claim 1, wherein said device accommodates use to bring scent to the user's hair by removing said atomizer spray bottle and wrapping said aroma device around the user's hair, creating a ponytail.

15. The wearable aroma emitting device of claim 1, further comprising an ornamental three dimensional stuffed structure attached to a portion of said tubular housing.

16. The wearable aroma emitting device of claim 15, wherein said ornamental three dimensional stuffed structure is made of porous material.

* * * * *